United States Patent [19]

Adams, Jr. et al.

[11] 4,189,304
[45] Feb. 19, 1980

[54] DEVICE AND METHOD FOR DETECTING MYOGLOBIN

[75] Inventors: Ernest C. Adams, Jr., Elkhart; Kathleen M. Layman, New Paris, both of Ind.

[73] Assignee: Miles Laboratories, Inc., Elkhart, Ind.

[21] Appl. No.: 955,452

[22] Filed: Oct. 27, 1978

[51] Int. Cl.² .................. G01N 33/16; G01N 31/22
[52] U.S. Cl. ............................... 23/230 B; 422/56
[58] Field of Search ............... 422/56, 57; 23/230 B

[56] References Cited

U.S. PATENT DOCUMENTS

| | | | |
|---|---|---|---|
| 3,290,117 | 12/1966 | Adams, Jr. | 23/230 B X |
| 3,699,003 | 10/1972 | Kronish | 422/56 X |
| 3,723,064 | 3/1973 | Liotta | 422/56 X |
| 3,868,219 | 2/1975 | Hurenkamp | 422/56 |
| 3,875,014 | 4/1975 | Forgione | 422/56 X |
| 3,915,639 | 10/1975 | Friedenberg | 422/56 X |
| 3,975,161 | 8/1976 | Svoboda | 422/56 |
| 4,017,261 | 4/1977 | Svoboda | 23/230 B X |
| 4,071,317 | 1/1978 | Lam | 23/230 B X |
| 4,071,321 | 1/1978 | Lam | 23/230 B X |
| 4,094,647 | 6/1978 | Deutsch | 422/56 |

OTHER PUBLICATIONS

Chemical Abstracts, 62: 940b, (1965).

*Primary Examiner*—Sidney Marantz
*Attorney, Agent, or Firm*—Roger N. Coe

[57] ABSTRACT

A test device and method for detecting myoglobin in the presence of hemoglobin in a fluid test sample. The test device comprises a chromatographic medium incorporating serum, haptoglobin and/or antiserum which binds or retards hemoglobin while permitting myoglobin to traverse the length of the test device. A test sample of body fluid is placed in contact with an appropriate portion of the chromatographic medium of said test device; hemoglobin in the body fluid is retained or retarded by the serum, haptoglobin and/or antiserum; and myoglobin in the sample traverses the length of the medium and contacts reagent means at a predetermined location thereon, resulting in a detectable response thereat.

11 Claims, 6 Drawing Figures

DEVICE AND METHOD FOR DETECTING MYOGLOBIN

FIELD OF THE INVENTION

The present invention relates to a test device and method useful in the diagnosis of myocardial infarction and, more particularly, to a test device and method for detecting myoglobin in the presence of hemoglobin.

BACKGROUND OF THE INVENTION

Occlusive vascular disease culminating in coronary thrombosis and myocardial infarction is epidemic in our modern industrialized society. Among striving, stressed, middle age executives in the United States, for example, the disease accounts for more than fifty percent of all hospitalizations and more than thirty percent of all deaths.

Since the classical features of coronary heart attack have been so widely publicized, it is seldom realized that early and accurate diagnosis is frequently quite difficult. Only a minority of patients have electrocardiographic findings which are dramatically clear cut. All too often, when a coronary patient is first seen by a physician, the patient's history is garbled, the symptoms are distorted, the physical findings are inconclusive and the electrocardiogram is unhelpful. When retrospective analyses of serial electrocardiograms on patients with myocardial infarction are undertaken, it is almost invariably possible to discern changes from the initial (or presenting) EKG which may be interpreted as early indications of cardiac damage. This type of analysis permits a whole pattern of progressive and retrogressive EKG changes to be examined at once. But in actual practice, when the presenting EKG is taken within twelve hours of an acute attack, it is possible to recognize changes pathognomonic of an infarct in only about one-third of the cases in which the condition actually occurs. In addition, it should be noted that EKG abnormalities may occur in the absence of disease of any kind and that changes not significantly different from those of infarction may accompany anginal attacks, pericarditis, pulmonary embolus and several other conditions that may give rise to clinical uncertainty.

Physical and laboratory findings consistent with tissue necrosis are the rule rather than the exception in myocardial infarction. Fever, leucocytosis and elevation of the erythrocyte sedimentation rate (ESR) generally become apparent within 24 to 48 hours. Serum glutamic oxalacetic transaminase (SGOT) rises to a peak on the second or third day and, in the absence of an additional insult, falls fairly rapidly thereafter. Absolute values are not nearly as meaningful as sequential variations, however, and it must always be borne in mind that pulmonary embolus, liver disease, and a considerable number of other conditions may give rise to elevated SGOT values. Similarly, serum creatinine phosphokinase (CPK), lactic dehydrogenase (LDH), gamma glutamyl transpeptidase ($\gamma$-GTP), serum pyruvate kinase (SPK) and their several isoenzymes may show a variety of elevations and changes throughout the course of a nonfatal myocardial infarction. The strength of the enzymatic tests lies primarily in their usefulness for monitoring the severity of the disease and the patient's progress toward recovery. But, interesting as these substances are to the laboratory scientists, medical practitioners have found them wanting and the search continues for a diagnostically meaningful biochemical signature of cardiac muscle injury. The fact is that, when help is most needed clinically—at the time of differential diagnosis, hospital admission and primary care—the laboratory findings are frequently no less equivocal than the signs and symptoms of coronary thrombosis.

When the heart muscle is damaged, particularly when necrosis occurs, a substance called myoglobin is very rapidly released. Because of its molecular structure, myoglobin soon finds its way via the kidneys from the blood stream to the urine. In patients with myocardial infarction, urinary myoglobin excretion generally rises to a maximum in the first twelve hours, diminishes rapidly in 24 hours and ordinarily reverts to undetectable levels in less than five days. On account of the very transitory nature of measurable levels of myoglobin excretion, it might appear at first glance improbable that a quantitative test for the substance could compete with the conventional enzyme tests and EKGs as a guide to the extent of myocardial damage. But, on account of the unusual speed with which urinary myoglobin excretion follows cardiac muscle injury, it does provide a reliable "yes-no" test and, when set at an appropriate level of sensitivity, it can serve as an extremely useful aid to the diagnosis of myocardial infarction. This is true even though urinary myoglobin excretion is not exclusive to myocardial infarction and may be associated with muscular dystrophy, crush (wringer) type injuries, alcoholism, epileptic seizures and a number of other conditions (most of which are quite readily distinguishable clinically from cardiac muscle damage).

A sensitive urinary myoglobin test can also bring to light subclinical infarcts that might otherwise be passed off as severe anginal attacks. Since these "occult" or mini-infarcts are believed to be often the progenitors of a more extensive and possibly fatal infarct-to-come, their detection could serve as a signal for the prompt institution of strict bed-rest and other therapy calculated to avert an impending disaster. Another possible use of a urinary myoglobin test is based on the theoretical likelihood that the substance may be released from skeletal muscle in cases of deep vein thrombosis. Thus, in nonsurgery associated cases the test could very well facilitate differentiation of this difficult-to-diagnosis infliction from other conditions. Accordingly, a need has existed for the development of a urinary myoglobin test to serve as a meaningful diagnostic tool which would help to confirm the presence of cardiac muscle damage in suspect or equivocal cases of myocardial infarction. In particular, a quick, convenient "yes-no" test has been needed in place of the more cumbersome and sophisticated quantitative systems which have been used to date.

Both chemically and physically, myoglobin closely resembles the oxygen carrying blood pigment hemoglobin. The most significant difficulty with the detection of myoglobin in the presence of hemoglobin is that both myoglobin and hemoglobin will react with the usual reagents for detection of peroxidase-like substances which could otherwise be utilized for the detection of myoglobin.

SUMMARY OF THE INVENTION

In accordance with the present invention, a test device and method are provided for determining the presence of myoglobin in body fluids. The test device is composed of a matrix material capable of transporting a sample fluid therealong by capillarity, having a portion at a predetermined location for receiving the test sample and another portion at a predetermined location incorporated with reagent means sensitive to myoglobin for providing a detectable response. Between the sample receiving portion and the detection portion of the matrix material a retaining portion thereof is provided which has serum, haptoglobin, antiserum or a mixture thereof dried on or affixed thereto. Thus, when a test sample containing both myoglobin and hemoglobin is applied to the receiving portion, the hemoglobin will be retained or retarded by the retaining portion of the test device, whereas the myoglobin is transported with the sample to the detection portion where it reacts with a reagent to produce a detectable response, such as a color change. In use, a test sample of body fluid, and particularly urine, is contacted with a contact or receiving portion of the test device, hemoglobin present in the body fluid is retained or retarded by the retaining portion before reaching the detection portion of the test device, and myoglobin present in the body fluid traverses the length of the test device and produces a detectable response upon contact with reagent in the detection portion of the test device.

BRIEF DESCRIPTION OF THE DRAWINGS

Other and further features of the invention will be apparent to those skilled in the art from the following detailed description, thereof, taken in conjunction with the accompanying drawings, in which.

DESCRIPTION OF THE PREFERRED EMBODIMENTS

The test devices of the present invention are typically composed of at least three portions of a suitable chromatographic medium, viz., a sample contacting portion, a retaining portion and a detection portion. In a convenient and preferred embodiment the chromatographic medium is in the form of a matrix affixed to a suitable support providing a handle facilitating use of the test device. The chromatographic medium, however, can take the form of particles or gel arranged in column format.

Figure 1:
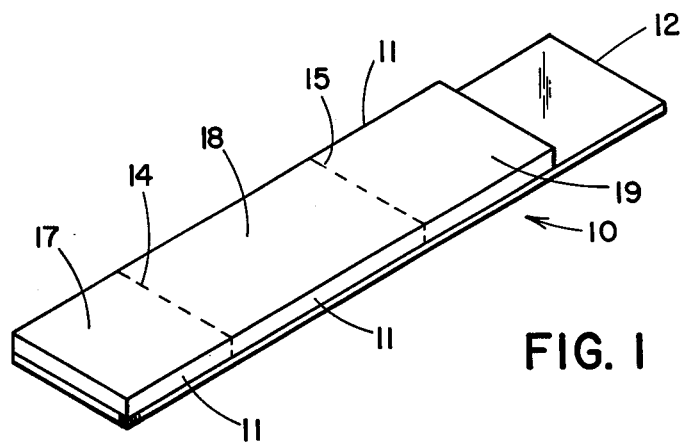
FIGS. 1 and 3 are perspective views of preferred forms of the test device of the present invention.
Figure 2:
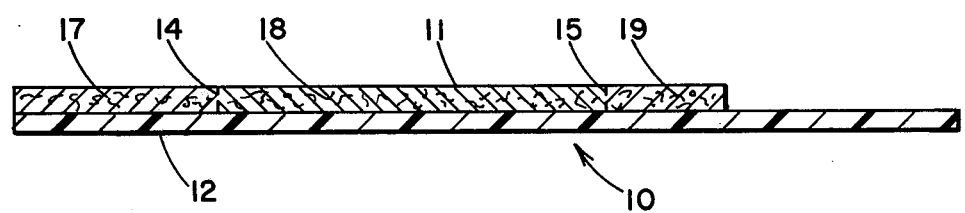
FIG. 2 is a longitudinal vertical cross sectional view of the test device of FIG. 1.

Referring to FIGS. 1 and 2, a test device 10 in accordance with the present invention is illustrated. Test device 10 is shown having a suitable elongated matrix 11 attached to support or backing member 12 extending beyond matrix 11 to serve as a handle for the test device. In addition, member 12 serves to provide rigidity to matrix 11.

For purposes of illustration test device 10 is shown in FIGS. 1 and 2 having matrix 11 with broken lines 14 and 15 defining three separate areas or portions, i.e., a sample receiving or contacting portion 17, a retaining portion 18 and a detection portion 19. The retaining portion 18 is treated to bring about the separation of myoglobin and hemoglobin in a sample liquid as said liquid passes by capillary action from sample contacting portion 17 to detection portion 19. The detection portion 19 contains a reagent, such as a peroxidase detection system, which is capable of producing a detectable response when contacted by myoglobin.

Figure 3:
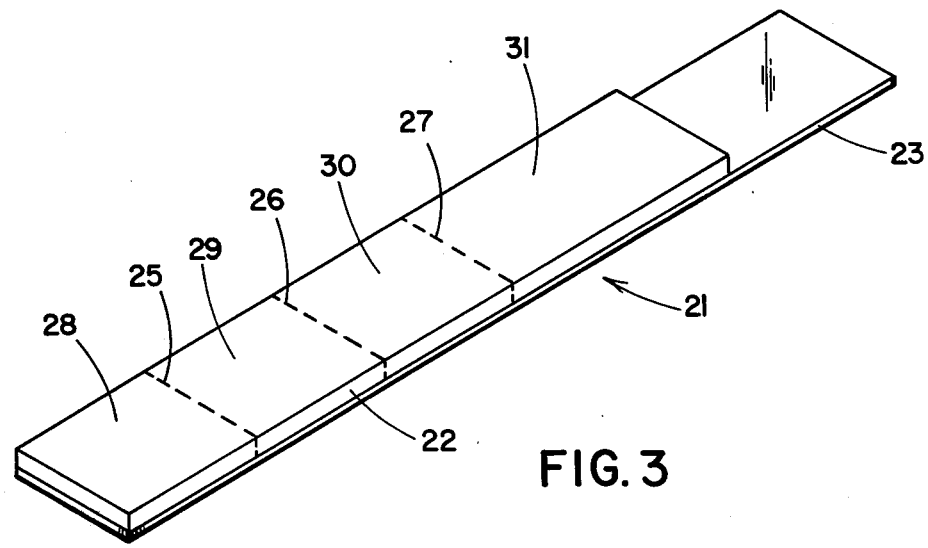

Another embodiment of the present invention is illustrated in FIG. 3 wherein a test device 21 is shown having an elongated matrix 22 attached to a support member 23. In FIG. 3 broken lines 25, 26, and 27 define matrix portions 28, 29, 30 and 31. Basically, portion 28 corresponds to sample receiving or contacting portion 17 of FIG. 1, portion 29 corresponds to retaining portion 18 of FIG. 1 and portion 31 corresponds to detection portion 19 of FIG. 1. Portion 30 of FIG. 3 constitutes a zone between portion 29, which has a retaining material affixed to matrix 22, and portion 31, which has reactive material affixed to matrix 22. If desired, portion 28 or portion 30 of matrix 22 can be treated to provide a matrix area having ion exchange characteristics. Alternatively, the matrix portions 28 or 30 can be comprised of ion exchange paper or other suitable ion exchange material. The presence of ion exchange characteristics in a portion of the matrix tends to prevent ascorbic acid and other known inhibitors sometimes present in test samples from reaching reactive portion 31, at least in amounts which might interfere with the desired reaction.

Figure 4:
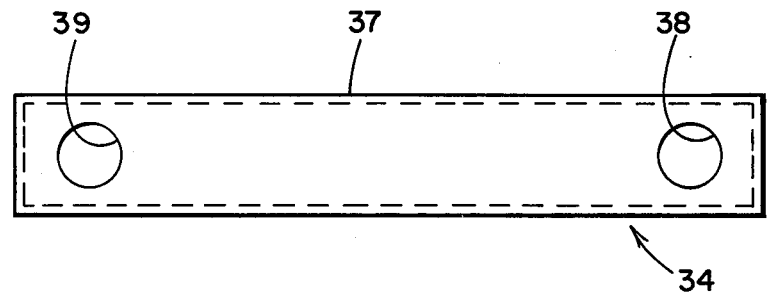
FIG. 4 is a top view of another form of a test device in accordance with the present invention.
Figure 5:
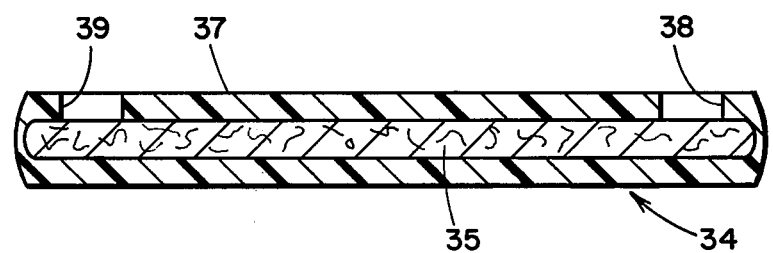
FIG. 5 is a longitudinal vertical cross sectional side view of the test device of FIG. 4.

FIGS. 4 and 5 are diagrammatic illustrations of yet another embodiment of the present invention. These figures illustrate a test device 34 comprising an elongated matrix 35 encased inside an organoplastic sheath 37. Matrix 35 can have a configuration similar to matrix 11 in FIGS. 1 and 2 or matrix 22 of FIG. 3. Sheath 37 contains two openings, 38 and 39, for the introduction of liquids and observation of the color change of the indicator system, respectively. Opening 38 can be at any suitable location which will permit contact between a sample fluid and the receiving portion of matrix 35. Normally, opening 38 is located at or near one end of test device 34 and opening 39 is located at or near the opposite end. Obviously, by using a thin film or essentially transparent plastic material for sheath 37 it is possible to eliminate any necessity for a window or opening 39 through which the indicator or reactive portion of matrix 35 can be observed.

Figure 6:
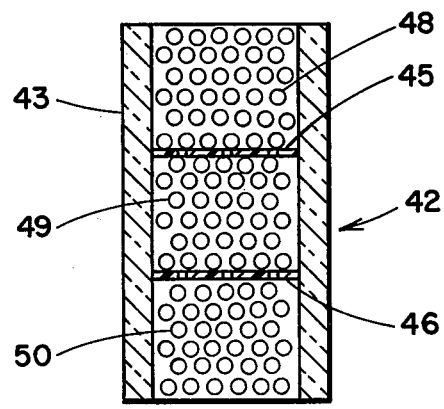
FIG. 6 is an axial cross sectional view of a columnar form of test device in accordance with the present invention.

FIG. 6 represents still another embodiment of the invention. In this embodiment a test device 42 comprises a column 43 filled with a suitable particulate medium such as acrylamide gel, Sephadex (trademark of Pharmacia Fine Chemicals, Inc.), Sepharose (trademark of Pharmacia Fine Chemicals, Inc.), and the like. Liquid permeable discs 45 and 46 separate the medium into sections, i.e., a sample receiving section 48, a retaining section 49 and a detection section 50. Particles in section 49 are treated with serum, haptoglobin or antiserum, and a suitable indicating system is used to treat the particles in section 50. Thus, the test device 42 of FIG. 6 is similar to test devices of FIGS. 1 through 5, differing only in that it is designed to function in a column format such that a test sample poured into section 48 flow by gravity through section 49 to section 50. An advantageous feature of the column format illustrated in FIG. 6 is the fact that when Sephadex and/or acrylamide particles are used, they tend to aid in the removal of materials which would otherwise interfere with the detection of myoglobin.

In the method of using the test devices illustrated in FIGS. 1 through 6, test solution is applied to a sample contacting portion of each test device, and after a predetermined time interval has elapsed, the time interval being appropriate to the particular test device, a determination is made in the detection portion of the device for some detectable response. Thus, the reaction proceeds in accordance with the following equation in the presence of haptoglobin:

Myoglobin + Hemoglobin 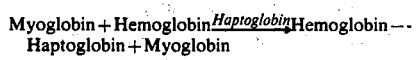 Hemoglobin — Haptoglobin + Myoglobin

Conventionally, the response of myoglobin, free of hemoglobin, in the detection portion is a color formation or a color change. For example, when the portion 17 of test device 10 of FIG. 1 is dipped into a urine sample containing myoglobin and hemoglobin, the urine passes from portion 17 through retaining portion 18 where hemoglobin present in the sample is retained or retarded, and the myoglobin in the sample, free of hemoglobin, passes on, with the sample, to detection portion 19 where a change in color indicates a positive test for myoglobin. The amount of serum, haptoglobin and/or antiserum specific for hemoglobin is calculated to provide sufficient binding capacity in retaining portion 18 to prevent hemoglobin from reacting with the indicator system in detection portion 19.

The carrier matrix for the embodiments of FIGS. 1–5 can be made of any material which is insoluble in the test sample and which is capable of transporting the test sample by capillarity. The test device matrix typically is relatively flexible, but has sufficient wet strength to retain its shape when wet. Of course, it should be made of material which will not deleteriously affect interactions between the test sample and reagents. A particularly useful material for the test device matrix is bibulous paper, such as filter paper. However, other materials can also be used including various felts, cloths, gels, fleeces, membranes and films made of natural or synthetic substances including cellulose, wood, polypropylene and the like. While the length and width of the test device can vary widely, the thickness of the test device matrix is usually between about 0.008 inch (0.2 mm) and 0.04 inch (1.0 mm).

The support member 12 in FIGS. 1 and 2, the support member 23 in FIG. 3 and sheath 37 in FIGS. 4 and 5 provide mechanical strength for the matrixes attached thereto. In the forms of the invention shown in FIGS. 1 to 3 the test device matrix and inert support are joined in laminate fashion with both being of approximately equal width. The thickness of the inert support can vary depending on the rigidity of the material of which it is made. Exemplary materials are the various vinyl plastics as well as polyester, polycarbonate, methylmethacrylate polymer, polystyrene, polyethylene, polypropylene and waxed cardboard. The length of the inert support will vary depending on the desired configuration of the test device.

The retaining portion of each matrix or chromatographic medium is prepared by treating the same with serum, haptoglobin, antiserum or a mixture thereof. Any conventional way of applying these materials to the retaining portion can be employed. For example, dipping, spraying, and the like can be employed followed by appropriate drying. Similarly, the test reagent system can be applied to the detection portion of each matrix in like manner or by printing. If desired, the retaining portion and the detection portion can be separately treated before being combined with the sample contacting portion to form one continuous matrix or chromatographic medium.

Although any test reagent can be utilized as long as it undergoes a detectable change in the presence of an oxygen source, orthotolidine is a preferred indicator for use in the test reagent of the present invention. Other indicators comprise a variety of organic materials, principally those of aniline and phenol derivation. To name but a few, orthotoluidine, tetramethyl orthotoluidine, paratoluidine, orthophenylenediamine, tetramethylbenzidine, N, N'-dimethyl-p-phenylenediamine, N, N'-diethyl-p-phenylenediamine, benzidine, p-anisidine, di-anisidine, o-cresol, m-cresol, p-cresol, α-napthol, β-napthol, catechol, guaiacol and pyrogallol can be used. In addition to the indicator, the test reagent preferably contains a quinoline derivative as a potentiating agent, such quinoline being substituted in the 4, 6 or 7 position. By way of specific example, suitable potentiating agents include quinoline; quinine; 6-methoxyquinoline; 4, 6-dimethylquinoline; 6-methylquinoline; 7-methylquinoline; 2, 6-dimethylquinoline, 2-methylquinoline; 8-amino-6-methoxyquinoline; 6-methoxy-3-phenylthioquinoline; 8-methylquinoline; 2, 3-dimethylquinoline; 2-quinolinol; 2-methyl-8-quinolinol; 8-quinolinol; 6-nitroquinoline; 1-ethyl-6-nitroquinoline; and 3-methyl-6-nitroquinoline.

Other additives, such as buffer and the like, can be employed in the test reagent. For example, emulsifying agents which can be used include polyvinyl alcohol, gum arabic, carboxyvinyl polymer and the like. Surfactants and wetting agents can also be used. In a preferred embodiment sodium lauryl sulfate or diocytl sodium sulfosuccinate is used as a wetting agent. By way of example, useful buffering systems include tartrate, phosphate, phthalate, citrate and acetate buffer. The preferred range of hydrogen ion concentration to which the test reagent composition is buffered is about pH 4 to pH 7. Specific examples of preferred test reagent systems are those set forth in U.S. Pat. No. 3,290,117 and U.S. Ser. No. 919,869, filed June 28, 1978, (assigned to the present assignee), which are hereby incorporated by reference.

The invention is further illustrated by the following examples.

EXAMPLE 1

A test device like that illustrated in FIG. 3 is made by forming a solution of haptoglobin [1 milligram per milliliter (mg/ml) in 0.15 molar (M), pH 7.4 phosphate] and adding the solution to filter paper by immersing the filter paper into the solution and then drying the filter paper. The filter paper is then cut into strips and applied as matrix portion 29 (in FIG. 3) to a polystyrene substrate together with untreated filter paper in matrix portions 28 and 30. The detection portion 31 is prepared by incorporating filter paper with the peroxidase detection reagent system set forth in Example 10 of U.S. Pat. No. 3,290,117.

When sample contacting portion 28 of matrix 22, as illustrated in FIG. 3, is wetted by dipping into a urine solution containing myoglobin and hemoglobin it is found that the hemoglobin is retained in matrix portions 29 and 30, whereas myoglobin flows with the sample through these portions and into the detection portion 31, causing a color change therein, i.e. a blue color is generated.

EXAMPLE 2

A test device is made which is identical to that of Example 1 except that matrix portion 29 (as illustrated in FIG. 3) is formed by immersing diethylaminoethyl cellulose anion exchange paper into a solution of haptoglobin (1 mg/ml in water) and then washing the paper with saline and drying the paper.

EXAMPLE 3

Another test device is prepared following the procedure set forth in Example 1 except that a 1/20 dilution of an antiserum to hemoglobin (made in goat) is used in place of the haptoglobin.

EXAMPLE 4

Following the procedure of Example 1 the filter paper in matrix portion 30 (FIG. 3) is replaced with anion exchange paper. The resulting test strip tends to remove ascorbic acid and other inhibitors, making the test device more sensitive.

EXAMPLE 5

Two grams (g) of cyanogen bromide activated Sepharose is suspended in 20 ml, 0.001 N HCl. After ten minutes the suspended material is washed with 600 ml of 0.001 N HCl on a sintered glass filter.

A 4.8% haptoglobin in water solution is prepared and 2 ml is added to 10 ml 0.2 M, 6.5 pH citrate. The resulting haptoglobin solution is mixed with the washed activated Sepharose and reacted overnight with end-over-end tumbling at 4° C. The resulting product is collected on a sintered glass filter, washed with 0.2 M, 6.5 pH citrate until the absorbance of the washings at 280 nanometers (nm) is less than 0.1, and then washed with saline until the absorbance at 215 nm is less than 0.1.

A test device, like test device 42 of FIG. 6, is prepared by filling sample receiving section 48 with Sepharose particles, filling retaining section 49 with activated Sepharose particles prepared as described above, and filling detection section 50 with Sepharose particles prepared by treating the particles with the indicator system of Example 11 in U.S. Pat. No. 3,290,117.

The resulting column test device is used by pouring a test sample into sample receiving section 48 and allowing the sample to flow by gravity through section 49 to section 50.

It will be understood that, if desired, test devices like those of FIGS. 1-4 can be made by embedding into paper as the chromatographic medium Sepharose prepared as described for use in the respective sections of the test device of FIG. 6.

The dimensions of the test device, the orientation of the sample receiving portion and the orientations of the retaining portion and the portion or portions incorporated with reagent can obviously be varied.

Obviously, many other modifications and variations of the invention as hereinbefore set forth may be made without departing from the spirit and scope thereof.

What is claimed is:

1. A test device for detecting myoglobin in the presence of hemoglobin in a fluid test sample, said test device comprising a chromatographic medium having a sample contacting portion, a retaining portion, and a detection portion incorporating a reagent capable of producing a detectable response when contacted with myoglobin, wherein said retaining portion of said chromatographic medium incorporates serum, haptoglobin, antiserum for hemoglobin or a mixture thereof.

2. The test device according to claim 1 in which the retaining portion of said chromatographic medium incorporates serum affixed to said medium.

3. The test device according to claim 1 in which the retaining portion of said chromatographic medium incorporates haptoglobin affixed to said medium.

4. The test device according to claim 1 in which the retaining portion of said chromatographic medium incorporates antiserum for hemoglobin affixed to said medium.

5. The test device according to claim 1 in which the detectable response produced by the reagent is a color change.

6. A test device for detecting myoglobin in the presence of hemoglobin in a fluid test sample, said test device comprising a chromatographic medium having a sample contacting portion, a retaining portion, and a detection portion, wherein said retaining portion of said chromatographic medium incorporates serum, haptoglobin, antiserum for hemoglobin or a mixture thereof affixed to said medium and wherein said detection portion of said chromatographic medium incorporates a reagent for detection of peroxidase-like substances.

7. A test device for the detection of myoglobin in a test sample containing hemoglobin, which comprises:
a length of capillary matrix having a first and second end;
a first zone located in said length of capillary matrix extending from the first end of the matrix for contact with a test sample;
a second zone located in said length of capillary matrix in the direction of said second end from said first zone;
a first reagent incorporated with said matrix in said second zone and adapted to slow or prevent capillary movement through said second zone of hemoglobin present in the test sample;
a third zone located in said length of capillary matrix extending from the second end toward the second zone; and
a second reagent incorporated with said matrix in said third zone and a adapted to provide a detectable response when contacted with myoglobin.

8. The test device of claim 7 in which the first reagent is haptoglobin.

9. The test device of claim 7 in which the first reagent is serum.

10. A method for detecting myoglobin in the presence of hemoglobin in a fluid test sample, comprising contacting the sample contacting portion of the test device of claim 1 with a fluid test sample containing hemoglobin and suspected of containing myoglobin, and observing any detectable response in the detection portion of said test device.

11. A method for detecting myoglobin in the presence of hemoglobin in a fluid test sample, comprising contacting the sample contacting portion of the test device of claim 5 with a fluid test sample containing hemoglobin and suspected of containing myoglobin, and observing any color change in the detection portion of said test device.